(12) United States Patent
Kloeffel

(10) Patent No.: US 9,265,874 B2
(45) Date of Patent: Feb. 23, 2016

(54) PRODUCTION OF INDIVIDUAL CONCENTRATE

(75) Inventor: Peter Kloeffel, Nuedlingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 570 days.

(21) Appl. No.: 13/346,065

(22) Filed: Jan. 9, 2012

(65) Prior Publication Data

US 2012/0181230 A1  Jul. 19, 2012

Related U.S. Application Data

(60) Provisional application No. 61/457,131, filed on Jan. 10, 2011.

(30) Foreign Application Priority Data

Jan. 10, 2011 (DE) .......................... 10 2011 008185

(51) Int. Cl.
*B01D 61/26* (2006.01)
*A61M 1/14* (2006.01)
*A61M 1/16* (2006.01)

(52) U.S. Cl.
CPC ....... *A61M 1/1656* (2013.01); *A61M 2205/505* (2013.01)

(58) Field of Classification Search
CPC ..................... A61M 1/1656; A61M 2205/505; B01F 15/00032
USPC ................. 210/645, 646, 647, 136, 143, 252, 210/257.1, 258, 321.71; 422/601, 682, 722; 514/23

See application file for complete search history.

(56) References Cited

U.S. PATENT DOCUMENTS 5,326,476 A       7/1994  Grogan et al.
6,139,754 A  *   10/2000  Hartranft et al. .............. 210/739
8,671,996 B2 *   3/2014   Weilhoefer et al. ............. 141/65

FOREIGN PATENT DOCUMENTS

| CN | 1638852 | 7/2005 |
|---|---|---|
| CN | 101622021 | 1/2010 |
| DE | 32 24 823 | 1/1984 |
| DE | 3224823 | 1/1984 |
| DE | 41 13 032 | 11/1991 |
| DE | 10313965 | 10/2004 |
| DE | 102007009269 | 8/2008 |
| DE | 102009031473 | 5/2011 |

(Continued)

OTHER PUBLICATIONS

English translation DE 10313965 B3 (Oct. 2004).*

(Continued)

*Primary Examiner* — John Kim
(74) *Attorney, Agent, or Firm* — Jacobson Holman, PLLC.

(57) ABSTRACT

A method provides for the production of a concentrate for dialysis, the composition of which can be adapted individually to the respective needs of the patient. The special components required individually are added in the form of highly concentrated special concentrates with a volume of 10-500 mL to 3-10 liters of standard concentrate. The two solutions are then mixed thoroughly by compressed air, which is blown through a concentrate intake rod into the solution from a compressed air source in the dialysis machine.

18 Claims, 1 Drawing Sheet

(56) References Cited

FOREIGN PATENT DOCUMENTS

| | | |
|---|---|---|
| EP | 1 485 145 | 7/2008 |
| WO | WO 99/07419 | 2/1999 |
| WO | WO 03/075982 | 9/2003 |
| WO | WO 2011/000347 A1 * | 1/2011 |

OTHER PUBLICATIONS

English translation WO 2011/000347 A1 (Jan. 2011).*

* cited by examiner

PRODUCTION OF INDIVIDUAL CONCENTRATE

CROSS-REFERENCE TO RELATED APPLICATIONS

This is a complete application claiming benefit of U.S. provisional application No. 61/457,131, filed Jan. 10, 2011, which claims the priority of German number 10 2011 008 185.2 filed Jan. 10, 2011, hereby incorporated by reference.

BACKGROUND OF THE INVENTION

1. Field of Invention

The invention relates to a method for producing an individual concentrate for dialysis with a device that includes a dialysis machine having a compressed air source, a concentrate line, a compressed air line between the concentrate line and the compressed air source, and a concentrate intake rod that is connected to the concentrate line. The method includes thoroughly mixing the first liquid concentrate and the second liquid concentrate in the container by introducing compressed air through the compressed air line, the concentrate line, and the connected concentrate intake rod. The invention also relates to a suitable device for performing the method. The composition of this individual concentrate may be adapted optimally to the specific needs of an individual patient without having to keep a large selection of concentrates on hand in the clinic. Through a system of concentrates that are mixed by machine in an automated process, the labor for the operating personnel and the risk of contamination are reduced.

2. Description of the Prior Art

In the treatment of chronic renal failure, solutions for hemodialysis are often prepared online from concentrates and ultrapure water by a portioning unit of the dialysis machine. The dialysis machine usually receives ultrapure water from a central supply, whereas the required electrolytes in the form of concentrates that are packaged in bags or canisters are made available on the dialysis machine by the nursing staff.

With the bicarbonate dialysis which is customary today, two concentrates are usually needed due to the required electrolyte composition of the solution for hemodialysis or similar methods, namely a basic concentrate which contains the buffer bicarbonate and optionally salt and an acid concentrate which contains the other electrolytes, for example, magnesium, calcium, potassium, glucose and an acid. The basic concentrate is usually supplied as a dry concentrate but may also be made available in the form of a liquid concentrate. The acid concentrate is usually a liquid concentrate. Liquid concentrates are usually supplied in plastic canisters with a volume of 3-10-L canisters. The two concentrates are drawn into the dialysis machine by the concentrate pumps of the portioning unit of the dialysis machine and are diluted with water in a defined ratio in the machine to obtain the desired electrolyte concentration. The resulting electrolyte solution corresponds largely to the composition of physiological, i.e., healthy blood plasma and can then be used for treatment of chronic renal failure by hemodialysis.

Renal failure can be triggered by a number of diseases. In addition, the dialysis treatment itself constitutes a serious intervention in the human body which may cause various complications and co-morbidities. Therefore, the initial situation at the beginning of treatment may vary greatly from one patient to the next. For example, many patients have extremely high potassium levels prior to dialysis. To make dialysis as gentle as possible, the potassium concentration in the dialysate may also be set somewhat higher here. The same thing is also true of the other electrolytes. Whereas most dialysis patients are found to have an excessive phosphate burden, many patients who have undergone dialysis suffer very intensely from hypophosphatemia, which can be relieved by the presence of phosphate in the dialysis solution. Malnutrition is another challenge dialysis patients must often encounter. An improvement can be achieved here by adding glucose or amino acids to the concentrate. In addition, the unintentional removal of trace elements from the blood due to the dialysis treatment can be counteracted, if necessary, by replacement of these trace elements in the dialysis solution. The individual requirements of the precise composition of the dialysis solution used thus cover a wide spectrum, and the individual adaptation of the dialysis solution to the respective needs of the patient can minimize adverse effects and improve the success of the treatment.

On the other hand, storage capacity in a clinic is limited, so that it is only possible to keep on hand a limited number of different dialysis concentrates. At the same time, storing and preparing a great many different concentrates would necessitate complex logistics.

DE 32 24 823 solves this problem by having a modular composition for the concentrate for the solution for hemodialysis. One or more special concentrates as an extra solution containing the desired extra components are added to a stock solution in which the electrolyte composition corresponds approximately to the physiological electrolyte composition of blood, after being diluted by the portioning unit of the dialysis machine. The stock solution is kept in a canister in an amount of nine liters. The extra solutions and/or special concentrates are added in amounts of 10-500 mL. The special concentrates each contain only one component, which is either not present in the stock solution or whose concentration is to be increased in comparison with that of the stock solution.

WO 99/07419 describes the addition of vitamins and trace elements to the liquid bicarbonate concentrate.

However, the concentrate for preparing the solution for hemodialysis must be homogeneous; otherwise safe handling is not ensured. Therefore, in practice today the resulting solution is mixed by intense agitation of the canister by the nursing staff after adding the special concentrate to the acidic or basic concentrate for the bicarbonate dialysis. This means a physical burden for the user. The canister must be opened to add the special concentrate. Before shaking the canister, it must be resealed with the cover. These steps may result in contamination of the concentrate.

SUMMARY OF THE INVENTION

The object of the invention is to prepare a specially adapted individual concentrate for the respective patient from at least one first concentrate and one second concentrate, so that the effort for the personnel and the risk of contamination are minimized while at the same time thorough mixing is ensured. Another object of the invention is to provide a device for producing an individual concentrate.

According to the teaching of the invention, these tasks are achieved by a method for preparing an individual liquid concentrate for dialysis, and a device for performing the method, both as they are described herein. Advantageous embodiments of the invention are described herein.

According to the teaching of the invention, this object is achieved by a method for preparing a liquid individual concentrate for dialysis such that the concentrate is in a container and is prepared from a first concentrate and at least one second concentrate by means of a device comprising a dialysis machine having at least one compressed air source, at least one compressed air line between the concentrate line and the compressed air source and at least one concentrate intake rod, which is connected to the concentrate line, so that the mixing of the two concentrates is accomplished by compressed air, which is introduced from the compressed air source in the dialysis machine through the compressed air line, the concentrate line and the connected concentrate intake rod into the container.

Before the start of treatment, the composition of the individual concentrate for the individual patient and the first concentrate and the second concentrate required for that as well as optionally additional concentrates are also determined.

Of the concentrates used in this method, the first concentrate is preferably a standard concentrate. In bicarbonate dialysis, two standard concentrates are needed, an acidic concentrate and a basic concentrate. Both the acidic and the basic concentrates may be used to perform the method according to the invention. To perform this method, conventional commercial liquid concentrates, e.g., AC-F Liquid 1+44 or BC-F liquid bicarbonate concentrate 8.4% from Fresenius Medical Care may be used for hemodialysis. The standard concentrate is preferably made available in an amount of 3-10 liters in a plastic canister but it may also be supplied in a bag or some other suitable container.

The second concentrate and possibly additional concentrates are preferably special concentrates which are supplied in an amount of 5-200 mL, preferably 10-50 mL. The concentrate ratios in the standard concentrate should not change for the other components due to the addition of the individual concentrate. The individual concentrates are therefore always added in the smallest possible amount of solution. Unlike the state of the art, it is then not necessary to adjust the volume.

The special concentrates preferably contain only one component per package unit, for example, potassium, sodium, calcium, magnesium or phosphate, glucose, vitamins, amino acids or trace elements. Any substance which is compatible with the components of the standard concentrate and should be administered to the patient or whose removal from the blood by dialysis is to be prevented may be used. The package unit may be a bag, a special cartridge or a solution drawn up into a syringe.

The special concentrate may be placed in the concentrate container for the standard concentrate, for example, because this is never filled completely. If the volume of the special concentrate, which tends to be low, is added to the much larger volume of the standard concentrate, this first yields a mixture that tends to be nonhomogeneous and is homogenized by the method according to the invention.

Before the start of the dialysis, the concentrate intake rod, which is connected to the concentrate line of the machine as a standard measure, is introduced into the concentrate container, which contains either pure standard concentrate or standard concentrate plus special concentrate. During the treatment, the concentrate intake rod serves to supply the concentrate with the help of a concentrate pump through a concentrate line to the portioning unit of the dialysis machine.

In the method according to the invention, air is introduced into the mixture of the concentrates through this concentrate intake rod and this mixture is then homogenized to form an individual concentrate. The air is supplied by a compressed air source, for example, a compressor in the dialysis machine. Such compressed air sources are often already provided in dialysis machines and are used, for example, to perform pressure tests or to set levels in air separation chambers. However, a compressed air source provided specifically only for this purpose may of course also be used.

The compressed air source supplies the compressed air to a compressed air line. According to one embodiment of the method according to the invention, a valve in the compressed air line is then opened and the compressed air goes from the air line into the concentrate line. The compressed air line is preferably connected to the concentrate line between the concentrate pump and the concentrate intake rod. From there, the compressed air is sent through the concentrate intake rod into the concentrate container, which contains the nonhomogeneous mixture of the concentrates. The outer end of the concentrate intake rod is situated near the bottom of the canister to enable the most thorough possible emptying during the removal of concentrate. The air emerging from the concentrate intake rod rises from the bottom to the surface in the form of air bubbles. These bubbles cause the concentrate to be homogenized, i.e., to be mixed thoroughly. In one embodiment of the method according to the invention, the compressed air is bubbled into the two concentrates at a rate of 1-10 L of air per minute over a period of 5-60 seconds. In an especially preferred method, before being bubbled into the mixture of the concentrates, the compressed air is sterile-filtered with the help of a sterile filter which is optionally installed in the compressed air line to minimize the risk of contamination.

The user can initiate performance of the method by input in the operating field of the dialysis machine, which is connected to a control unit. The input may be accomplished in various ways. The operating field may be a touchscreen, for example, on which the different treatment options can be selected by the user. This touchscreen may have an "air" button, which, when operated, signals to the control unit that the method according to the invention is to be performed. However, the signal may also be triggered by a mechanical button on the dialysis machine, which is operated by the operator as needed. The aforementioned method steps are then prompted by a control unit, which is configured to perform the method according to the invention, and these steps are optionally monitored.

To perform the method according to the invention, a device for performing a dialysis treatment and having a portioning unit may be used for online supply of solutions for hemodialysis with at least one concentrate line and with a concentrate intake rod connected thereto and with at least one compressed air source, such that this portioning unit has a compressed air line from the compressed air source to the concentrate line connected to the concentrate intake rod. Any commercial compressor capable of supplying a flow rate of 1-10 liters of air per minute may be used for this compressed air source.

In a preferred embodiment, the compressed air line also has a sterile filter, so that the air which is passed through the concentrate does not contaminate it. The sterile filter serves to sterilize the air used to mix the concentrates. The sterile filter may be, for example, a commercial membrane filter but any other filter suitable for sterile filtration may also be used.

In another preferred embodiment, a valve is provided at the connecting point of the compressed air line and the concentrate line. In a preferred embodiment, this is a nonreturn valve. In an especially preferred embodiment, this is an electromagnetic cutoff valve. However, any other valve suitable for separating the compressed air line from the concentrate line may also be used. The end of the concentrate line which leads out of the dialysis machine is connected to a concentrate intake rod. This concentrate intake rod is immersed in the concentrate container. To allow the most thorough possible emptying of the concentrate container, for example, a plastic canister, the outer end of the concentrate intake rod may be situated on the bottom of the container. From the end of the concentrate intake rod, the air is directed from the compressed air source into the canister containing the standard concentrate and the special concentrate, so that they become thoroughly mixed to form an individual concentrate.

Additional details and advantages of the invention are described in greater detail below on the basis of an exemplary embodiment depicted in the only drawing, in which:

BRIEF DESCRIPTION OF THE DRAWING

The sole drawing FIGURE shows a device for automatic thorough mixing of concentrates.

DETAILED DESCRIPTION OF THE PREFERRED EMBODIMENTS

Figure 1:
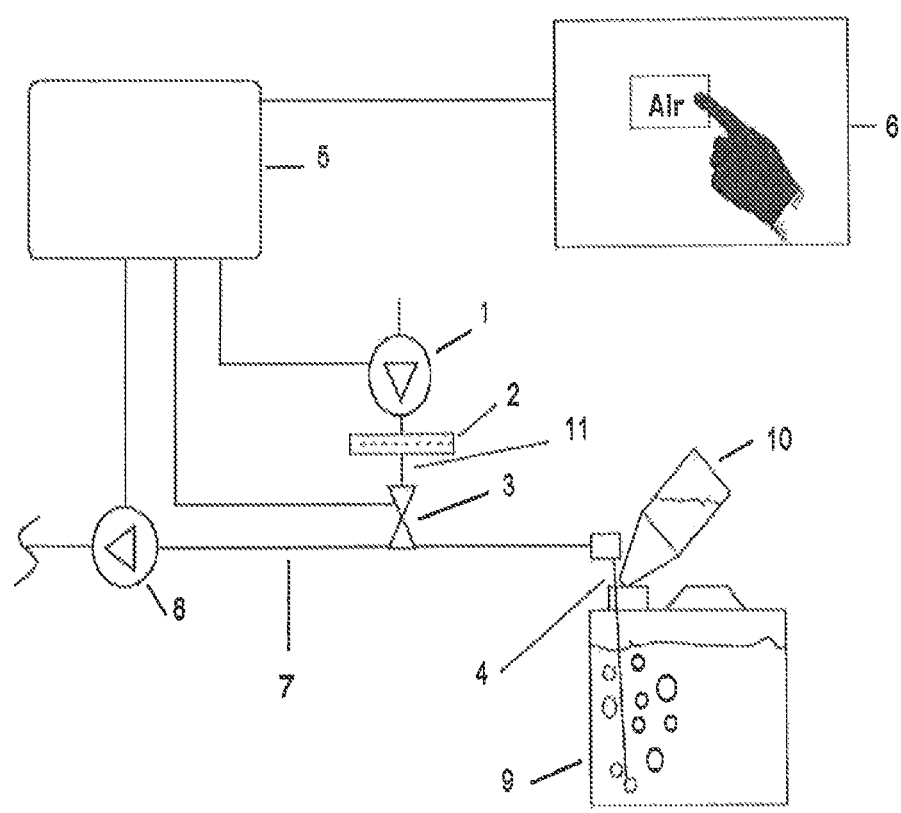

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

As described in state of the art, after the determination of the composition of the individual concentrate by the treating physician, required second concentrate, for example, a special concentrate 10, is added to the first concentrate, for example, the standard concentrate 9. For example, a 4.7-liter canister (1+44) AC-F 119/5 from Fresenius Medical Care is used here as the first concentrate and/or standard concentrate 9. The solution for hemodialysis obtained from this concentrate after dilution has a potassium chloride concentration of 1 mmol/L, which may be increased to 2 mmol/L by adding 50 mL of a special concentrate 10 having a KCl concentration of 4.2 mol/L to the standard concentrate 9.

The concentrate intake rod 4 is introduced into the resulting nonhomogeneous mixture of the concentrates. Since the concentrate is to be removed from the container as thoroughly as possible, the end of the concentrate intake rod is placed in the lower area of the container. The operator then signals to the control unit 5 of the dialysis machine by making an entry in an operating field 6 that the method for thorough mixing of the concentrates is to be performed. The control unit 5 then causes the compressed air source 1 to convey compressed air into the compressed air line 11 in an amount of 2 liters of air per minute, for example. At the same time, the electromagnetic cutoff valve 3 is opened. After the compressed air has been sterile-filtered by the sterile filter 2 in the compressed air line 1, it passes through the opened magnetic cutoff valve 3 into the concentrate line 7. The concentrate pump 8 is closed at this point in time and closes the concentrate line 7 in the direction of the portioning unit. The compressed air is then conveyed through the concentrate intake rod into the standard concentrate 9 to which the special concentrate 10 has been added and it thus homogenizes this mixture within 30 seconds, for example, to form an individual concentrate.

The method according to the invention allows an individual adaptation of the dialysis solution used to the needs of the individual patient without having to keep on hand a large number of different concentrates. The additional effort for the nursing personnel is minimal.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of producing an individual liquid concentrate in a container for dialysis from a first liquid concentrate and a second liquid concentrate with a device that includes a dialysis machine having a compressed air source, a concentrate line, a compressed air line between the concentrate line and the compressed air source, and a concentrate intake rod that is connected to the concentrate line, said method comprising:
   thoroughly mixing the first liquid concentrate and the second liquid concentrate in the container by introducing compressed air, the compressed air being introduced into the container from the compressed air source in the dialysis machine through the compressed air line, the concentrate line, and the connected concentrate intake rod.

2. The method according to claim 1, wherein the first liquid concentrate is a standard concentrate for a bicarbonate dialysis.

3. The method according to claim 2, wherein the standard concentrate is an acidic concentrate or a basic concentrate for the bicarbonate dialysis.

4. The method according to claim 2, wherein the standard concentrate is supplied in an amount of 3-10 liters.

5. The method according to claim 1, wherein the second liquid concentrate is a special concentrate.

6. The method according to claim 5, wherein the special concentrate is supplied in an amount of 5-200 mL.

7. The method according to claim 6, wherein the special concentrate is supplied in an amount of 10-50 mL.

8. The method according to claim 5, wherein the special concentrate includes potassium, sodium, calcium, magnesium phosphate, glucose, vitamins, amino acids, and/or trace elements.

9. The method according to claim 5, further comprising other special concentrates.

10. The method according to claim 1, wherein the compressed air source is a compressor.

11. The method according to claim 10, further comprising a valve located between the compressed air line and the concentrate line, and a step of opening the valve to supply the compressed air to the concentrate line.

12. The method according to claim 1, wherein the step of mixing includes introducing the compressed air into the first liquid concentrate and the second liquid concentrate in the container over a period of 5-60 seconds.

13. The method according to claim 1, wherein the compressed air is supplied in an amount of 1-10 liters of air per minute.

14. The method according to claim 1, further comprising a step of sterile-filtering the compressed air before introducing the compressed air into the concentrate line.

15. The method according to claim 1, further comprising a control unit, and wherein control and regulating processes for performing the method are associated with operation of the control unit.

16. A device for performing a dialysis treatment, comprising:
   a portioning unit for online supply of a first liquid concentrate and a second liquid concentrate for the dialysis treatment, the portioning unit including
   a liquid concentrate line,
   a concentrate intake rod connected to the liquid concentrate line, a source of compressed air for mixing of the first liquid concentrate and the second liquid concentrate, a compressed air line from the compressed air source to the liquid concentrate line connected to the concentrate intake rod, and a control unit configured to control and regulate processes associated with performing the dialysis treatment, including the mixing of the first liquid concentrate and the second liquid concentrate by introducing the compressed air through the compressed air line, the liquid concentrate line, and the connected concentrate intake rod.

17. A method of producing an individual liquid concentrate in a container for dialysis from a first liquid concentrate and a second liquid concentrate with a device that includes a dialysis machine having a compressed air source, a concentrate line, a compressed air line between the concentrate line and the compressed air source, and a concentrate intake rod that is connected to the concentrate line, said method comprising the steps of:

combining the first liquid concentrate and the second liquid concentrate in the container; and mixing the combined first liquid concentrate and second liquid concentrate in the container by introducing compressed air so as to produce a homogeneous individual liquid concentrate, the compressed air being introduced into the container from the compressed air source through the compressed air line, the concentrate line, and the connected concentrate intake rod.

18. The method according to claim 17, wherein the step of combining includes providing the first liquid concentrate in the container, and adding the second liquid concentrate thereto.

* * * * *